(12) United States Patent
Derks et al.

(10) Patent No.: US 6,365,761 B1
(45) Date of Patent: Apr. 2, 2002

(54) PROCESS FOR PREPARING ALKYLENE OXIDE

(75) Inventors: Willem Derks; Hendrik Dirkzwager, both of Amsterdam; Alexander Jan Van Der Veen; Rutger Johannes Franciscus Wermeling, both of Moerdijk, all of (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/590,549

(22) Filed: Jun. 8, 2000

(30) Foreign Application Priority Data

Aug. 18, 1999 (EP) .............................................. 99202670

(51) Int. Cl.[7] ......................... C07D 301/19; B01J 38/02; B01J 38/52; B01J 38/56; B01J 38/68
(52) U.S. Cl. ........................... 549/529; 502/20; 502/29; 502/30; 502/31; 502/33
(58) Field of Search ........................... 549/529; 502/20, 502/29, 30, 31, 33

(56) References Cited

U.S. PATENT DOCUMENTS

| | | | |
|---|---|---|---|
| 4,367,342 A | 1/1983 | Wulff et al. ................. | 549/529 |
| 5,798,313 A | 8/1998 | Carroll et al. ................. | 502/38 |
| 5,849,937 A | 12/1998 | Jubin, Jr. et al. ........... | 549/529 |

FOREIGN PATENT DOCUMENTS

| | | | | |
|---|---|---|---|---|
| EP | 0345856 | 5/1989 | ............ | B01J/21/06 |
| WO | WO 98/28072 | 11/1997 | ............ | B01J/21/20 |
| WO | WO 98/18555 | 5/1998 | | |
| WO | WO 99/01445 | 1/1999 | | |

OTHER PUBLICATIONS

International Search Report of Dec. 4, 2000.

Industrial Organic Chemistry, Second Revised and Extended Edition, Translated by Charlet R. Lindley, (1993), pp. 142–146 and 264–269.

*Primary Examiner*—Ba K. Trinh

(57) ABSTRACT

Process for the preparation of alkylene oxide, which process comprises passing a feed comprising an organic hydroperoxide and alkene through a bank of at least two serially connected reactors all containing a bed of heterogeneous epoxidation catalyst particles and operated in a cyclic mode, in which process:
(a) the first reactor of the cyclically operated bank is put in a position further down this bank, when the activity of the epoxidation catalyst contained therein has decreased to an undesirably low level;
(b) in this position the catalyst with decreased activity is contacted with the effluent from the reactor in the preceding position at a temperature which is at least 5° C. higher than the final temperature at which the catalyst was in use in the first position of the bank and for sufficient time to restore its activity to the desired level. The bank of cyclically operated epoxidation reactors may be followed by one or more additional fixed bed epoxidation reactors which are not operated cyclically.

14 Claims, No Drawings

PROCESS FOR PREPARING ALKYLENE OXIDE

1. FIELD OF THE INVENTION

The present invention relates to a process for the preparation of an alkylene oxide, more specifically, to a process for preparing an alkylene oxide from an alkene wherein the epoxidation reactors used are operated in such a way that the life of the epoxidation catalyst is significantly prolonged. The present invention also relates to a process for re-activating an at least partly deactivated heterogeneous epoxidation catalyst.

2. BACKGROUND OF THE TECHNOLOGY

The epoxidation of an alkene into alkylene oxide by reacting the alkene with an organic hydroperoxide is known in the art.

For instance, in the commonly known method for co-producing propylene oxide and styrene starting from ethylbenzene, the aforementioned epoxidation reaction is applied. In general this co-production process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenyl-ethanol, and (iii) converting the 1-phenyl-ethanol into styrene by dehydration using a suitable dehydration catalyst.

Another method for producing alkylene oxide is the coproduction of propylene oxide and methyl tert-butyl ether (MTBE) starting from isobutane and propene. This process is well known in the art and involves similar reaction steps as the styrene/propylene oxide production process described in the previous paragraph. In the epoxidation step tert-butyl hydroperoxide is reacted with propene forming propylene oxide and tert-butanol in the presence of a heterogeneous epoxidation catalyst. Tert-butanol is subsequently etherified with methanol into MTBE, which is used as an additive in motor fuels.

The present invention concerns the epoxidation reaction between an alkene and an organic hydroperoxide, and more in particular the epoxidation reaction, wherein use is made of a bank of serially connected fixed bed reactors, each filled with at least one bed of heterogeneous epoxidation catalyst, thereby particularly addressing the deactivation of this heterogeneous epoxidation catalyst.

Heterogeneous epoxidation catalysts are known in the art. Such catalysts may comprise as the catalytically active metal one or more transition metals, such as vanadium, molybdenum, tungsten, titanium and zirconium. One particularly suitable class of heterogeneous epoxidation catalysts are the titanium-based catalysts. Examples of such catalysts are for instance described in U.S. Pat. No. 4,367,342 and EP-A-0,345,856. U.S. Pat. No. 4,367,342 discloses the use of inorganic oxygen compounds of silicon in chemical composition with at least 0.1% by weight of an oxide or hydroxide of titanium, while EP-A-0,345,856 discloses a titania-on-silica heterogeneous catalyst. According to EP-A-0,345,856 this catalyst is obtainable by impregnating a silicon compound with a stream of gaseous titanium tetrachloride followed by calcination and hydrolysis steps and optionally a silylation step.

When such heterogeneous epoxidation catalysts are used to catalyse the epoxidation of an alkene, deactivation of the catalyst will occur. Without any preventive measures an epoxidation catalyst, which is contacted with a stream containing an alkene and an organic hydroperoxide from the preceding oxidation step, will have a limited lifetime due to deactivation and consequently will have to be replaced.

An increase of the lifetime of the catalyst would be beneficial, as it would result in a higher and more cost effective production of alkylene oxide. It would reduce the costs due to catalyst consumption and the time and costs involved in reloading of the reactors. Furthermore, an increased lifetime of the catalyst is desirable, because in that case the average reaction temperature could be kept lower, thus producing less by-products.

3. SUMMARY OF THE INVENTION

The present invention provides in a first aspect a process for the preparation of an alkylene oxide involving the cyclic operation of a bank of serially connected, fixed bed epoxidation reactors operated under certain conditions which have been found to significantly prolong the catalyst life. The process according to the present invention results in a re-activation of deactivated catalyst and hence in an increased lifetime of the catalyst. This, in return, results in a more cost effective and productive process.

Accordingly, the present invention relates to a process for the preparation of alkylene oxide, which process comprises passing a feed comprising an organic hydroperoxide and alkene through a bank of at least two serially connected reactors all containing a bed of heterogeneous epoxidation catalyst particles and operated in a cyclic mode, optionally followed by at least one additional epoxidation reactor containing a bed of heterogeneous epoxidation catalyst particles, and continuously withdrawing a product stream from the final epoxidation reactor comprising alkylene oxide and an alcohol as reaction products, from which product stream the alkylene oxide end-product is recovered, in which process:

(a) the first reactor of the cyclically operated bank is put in a position further down this bank or in a position directly after any one of the additional reactors, when the activity of the epoxidation catalyst contained therein has decreased to an undesirably low level;

(b) in this position the catalyst with decreased activity is contacted with the effluent from the reactor in the preceding position at a temperature which is at least 5° C. higher than the final temperature at which the catalyst was in use in the first position of the bank and for sufficient time to restore its activity to the desired level.

4. DETAILED DESCRIPTION OF THE INVENTION

A major advantage of the process according to the present invention is that the reactor containing the deactivated catalyst does not have to be taken out of operation each time the level of deactivation has become undesirably high, so that the process need not be interrupted each time the epoxidation catalyst in the first epoxidation reactor has deactivated. Furthermore, while being in its new position, the deactivated catalyst may still continue to contribute to the final alkylene oxide yield. Namely, while its activity is increasing, the amount of alkene converted into alkylene oxide over this specific catalyst bed may also increase. Cyclic operation of a bank of serially connected epoxidation reactors is known in the art. For instance, U.S. Pat. No. 5,849,937 discloses a method for operating a bank of serially connected epoxidation reactors for producing alkylene oxide, wherein the reactor containing the mostly deactivated catalyst is either in the first or in the terminal position and, when taken out of operation, is immediately replaced in respectively the terminal and first position by another reactor containing fresh catalyst. Accordingly, in this method a constant number of epoxidation reactors is continuously in operation while one reactor is in a standby position. Having one reactor on standby is considered undesired from a cost perspective.

In commercial operation the epoxidation reaction is typically carried out at temperatures of 50 to 135° C., suitably 70 to 125° C. and pressures up to 80 bar, suitably 10 to 60 bar, with the reaction medium being in the liquid phase. Normally there is a temperature increase in the reactor as the epoxidation proceeds. Therefore, cooling means are suitably present between each two subsequent epoxidation reactors. In order to compensate for the activity loss of the catalyst due to deactivation, the temperature in the reactor can be raised, e.g. by controlling the amount of cooling applied, so that the conversion in each reactor can be kept at the desired level. The temperature is raised until a temperature is reached above which one would expect the negative side-effects (e.g. the formation of by-products) to become unacceptable and the deactivation to be at such level that replacement of the catalyst is necessary. The maximum temperature reached during the epoxidation to compensate for the loss of activity of the catalyst is referred to as the "final temperature". This final temperature will normally be reached towards the end of an epoxidation cycle, i.e. the period between two subsequent reactor switches in the bank of epoxidation reactors plus possible additional epoxidation reactors.

Thus, in the process of the present invention the at least partly deactivated catalyst in the first reactor of the bank is subjected to a temperature which is at least 5° C. higher than the aforementioned final temperature. This is achieved by placing this first reactor in a position further down said bank or, if one or more additional epoxidation reactors are used, in a position directly after any one of the additional reactors and by contacting the deactivated catalyst with the effluent from the previous reactor at the required temperature.

Accordingly, in step (a) of the present process the first reactor of the cyclically operated bank is put in a position further down this bank or, if one or more additional epoxidation reactors are used, may also be placed in a position directly after any one of such additional reactors, when the activity of the epoxidation catalyst contained therein has decreased to an undesirably low level. In a very much preferred embodiment, however, the first reactor of the bank is put in the terminal position of the bank of cyclically operated reactors in step (a) irrespective of the presence of any additional reactor.

The bank of serially connected and cyclically operated epoxidation reactors consists of at least two fixed bed epoxidation reactors. However, it is preferred that this bank contains at least three reactors, while a preferred maximum number of reactors forming the bank is seven. Most preferably, said bank consists of three to five reactors.

After the bank of serially connected epoxidation reactors described above one or more additional fixed bed epoxidation reactors may be present. If more than one of such additional reactors are present, these reactors are suitably connected in series and are preferably not operated in a cyclic mode. If present at all, the number of additional reactors will suitably be from one to five, although from a cost perspective one to three additional reactors are preferred.

The reactor switch in step (a) takes place when the activity of the epoxidation catalyst contained therein has decreased to an undesirably low level. Normally, this will be the case when the catalyst has 20% or less of its original activity left. The term "original activity" refers to the activity of the catalyst at the start of the epoxidation cycle, i.e. directly after the previous reactor switch when the catalyst in question was taken in use while being in the reactor in the first position of the cyclically operated bank. Preferably, the reactor switch takes place when the catalyst only has 10% or less of its original activity left, more preferably less than 5% and most preferably less than 1%. However, the catalyst deactivation level may vary and may even be outside the ranges indicated above depending on factors like cooling capacity, number of reactors in the bank, presence of additional reactors, rate of deactivation and composition of the feed.

The actual reactor switch can be carried out by any suitable means known to the skilled operator and process engineer. Normally such means will comprise an adequate pipeline system with valves at the appropriate locations, so that the feed streams and effluent streams of the various reactors can be led to the desired places in the process.

In step (b) of the present process the catalyst with decreased activity is contacted in its new position with the effluent from the reactor in the preceding position at a temperature which is at least 5° C. higher than the final temperature at which the catalyst was in use in the first position of the bank and for sufficient time to restore its activity to the desired level. It has been found particularly advantageous if this temperature is at least 10° C. and preferably at least 15° C. higher than the final temperature at which the catalyst was in operation in the first position of the bank. More preferably, the temperature to which the at least partly deactivated catalyst is subjected is not more than 50° C. higher and more preferably not more than 30° C. higher than said final temperature. The period of time during which the (partly) deactivated catalyst is maintained at the elevated reactivation temperature should be sufficient to restore the activity of the catalyst to the desired level. Normally, this will not be less than 20 hours, because in that case insufficient reactivation would be accomplished. There is no fixed maximum to this time, because the reactor containing the catalyst to be reactivated remains in constant operation. Thus, the more the catalyst is re-activated the more this catalyst is able to convert alkene into alkylene oxide. If the reactor containing the re-activated catalyst remains in operation, then the time it remains in its new position is determined by the deactivation rate of the catalyst bed of the reactor which is then in the first position of the bank, because this is the catalyst next in line to be re-activated. If the reactor containing the re-activated catalyst is placed back in the first position of the bank of cyclically operated reactors, then the time it remains in its new position will suitably be at most 10 days, preferably at most 6 days.

The stream, with which the catalyst to be re-activated is contacted, is the effluent from a preceding epoxidation reactor. This effluent will anyhow contain propylene oxide and an alcohol (1-phenyl-ethanol in case the propylene oxide producing process forms part of a styrene/propylene oxide co-production process). In a styrene-propylene oxide co-production process this effluent will also contain ethylbenzene and normally also ethylbenzene hydroperoxide (EBHP). However, EBHP may be essentially absent if the reactor containing the deactivated catalyst is placed in the terminal position of the bank of cyclically operated reactors and no additional epoxidation reactors are used. This embodiment will be discussed in more detail hereinafter.

Accordingly, in one preferred embodiment of the present invention steps (a) and (b) of the present process are repeated until the activity of the catalyst to be re-activated can no longer be restored to the desired level. Furthermore, if re-activation can no longer be adequately effected it is preferred to take the reactor containing the catalyst which is mostly deactivated, out of operation, to replace the deactivated catalyst in this reactor by fresh catalyst and put this reactor back into operation in the terminal position of the bank.

In another preferred embodiment the process of the present invention comprises in addition to steps (a) and (b) the steps of:
(c) after the activity of the catalyst has been restored to the desired level, the reactor is put back in the first position of the bank;
(d) optionally steps (a) through (c) are repeated at least one time;
(e) the first reactor is taken out of operation when the activity of the epoxidation catalyst contained therein has decreased to an unacceptably low level and can no longer be restored to the desired level and the deactivated catalyst is replaced with fresh catalyst;
(f) this reactor is put back into operation in the terminal position of the cyclically operated bank; and
(g) steps (a) through (f) are repeated while a product stream containing alkylene oxide and an alcohol is continuously withdrawn from the last reactor.

In this embodiment the at least partly deactivated catalyst is put back in the first position of the bank as soon as its activity has been sufficiently restored.

If no additional epoxidation reactors beside the cyclically operated bank of epoxidation reactors is used, one particularly preferred way to carry out the latter embodiment is to place the first reactor containing the catalyst to be re-activated in the terminal position of the bank of reactors in step (a) and to increase the conversion level of the other reactors to a total of at least 95%, and most preferably to essentially 100%, based on EBHP. Consequently, the reactor containing the catalyst to be re-activated is then contacted with the effluent from the reactor in the second last position, which contains at most 5% EBHP and preferably is essentially free of EBHP. After at least 20 hours and preferably at most 10 days, more preferably at most 6 days, the catalyst will have been sufficiently re-activated and the reactor will be placed back in the first position (step (c)). Conversion conditions, in particular the temperature, will be adapted to achieve at least 95% EBHP conversion, and preferably essentially 100% EBHP conversion, over all reactors again. Steps (d) through (g) can then be carried out in line with the above procedure.

The process according to the present invention is applicable to heterogeneous epoxidation catalysts of all epoxidation reactions involving the reaction of an alkene with an organic hydroperoxide. Suitable organic hydroperoxides are secondary and tertiary hydroperoxides derived from a $C_4$–$C_{20}$ aliphatic hydrocarbon, a $C_7$–$C_{20}$ aralkyl hydrocarbon or mixtures thereof. Examples of suitable organic hydroperoxides include tert-butyl hydroperoxide, tertiary amyl hydroperoxide, tertiary octyl hydroperoxide, ethylbenzene hydroperoxide, cyclohexyl hydroperoxide and diethyl benzyl hydroperoxide. Of these, ethylbenzene hydroperoxide and tert-butyl hydroperoxide are most suitably applied.

The alkene used can be any organic compound having at least one aliphatic carbon-carbon double bond. Such compound will generally contain from 2 to 25 carbon atoms and preferably from 3 to 12 carbon atoms, such as propene, 1-butene, 2-butene, 1-pentene, 1-octene, 1-dodecene, styrene and methylstyrene. Most preferably, however, propene is used as the alkene, thus producing propylene oxide in accordance with the process of the present invention.

The heterogeneous epoxidation catalyst used may be any such catalyst known in the art to be suitable for catalysing the reaction between an alkene and an organic hydroperoxide into the corresponding alkylene oxide and alcohol. However, titanium-containing catalysts are preferred. Accordingly, the catalysts disclosed in the patent specifications U.S. Pat. No. 4,367,342 and EP-A-0,345,856 discussed above may, for instance, be applied. It has, however, been found particularly advantageous to use the titania-on-silica catalysts disclosed in EP-A-0,345,856 in all epoxidation reactors for the purpose of the present invention. When these catalysts are used, very good results are achieved by the present process.

The composition of the feed to the epoxidation reactor is not critical for the process of the present invention in the sense that it may have any composition which is common in commercial operation. Accordingly, in case of a styrene/propylene oxide co-production process, the feed to the epoxidation unit comprises at least some ethylbenzene hydroperoxide (EBHP) and normally also a substantial amount of ethylbenzene. Propene is either added to the reactor as a separate feed stream or may be added to the EBHP-containing feed stream prior to entry into the epoxidation reactor(s). The feed may also contain some methyl phenyl ketone and/or 1-phenyl-ethanol formed in the preceding oxidation section or in a preceding epoxidation reactor or contained in a recycle stream. A typical feed stream to the epoxidation reactor, which is first in line after the preceding oxidation step including oxidation reactor product work-up steps (like washing and distillation), comprises 15–25 wt % EBHP, 30–50 wt % ethylbenzene, 30–50 wt % propene, 0–5 wt % 1-phenyl-ethanol and 0–5 wt % methyl phenyl ketone, to a total of 100 wt %.

In a MTBE/propylene oxide co-production process the feed to the epoxidation reactor comprises at least some tert-butyl hydroperoxide (TBHP) in a tert-butanol solvent. Similar as in the styrene/propylene oxide co-production process, propene is either added to the reactor as a separate feed stream or may be added to the TBHP-containing feed stream prior to entry into the epoxidation reactor.

In a further aspect the present invention also relates to a process for re-activating an at least partly deactivated heterogeneous epoxidation catalyst capable of promoting the epoxidation reaction between an alkene and an organic hydroperoxide into alkylene oxide and an alcohol.

Such re-activation processes are known in the art. For instance, in WO 98/28072 a regeneration process for this type of catalysts is disclosed, which comprises contacting the used catalyst with a particular solvent at a temperature of from 20 to 400° C. This method has as a major drawback that the reactor containing the used catalyst has to be taken out of operation for the regeneration treatment to take place. Moreover, while being regenerated the catalyst does not contribute to the yield of end product.

In U.S. Pat. No. 5,798,313 a regeneration method for titanium-containing heterogeneous olefin epoxidation catalysts is disclosed, wherein the used epoxidation catalyst is heated at a temperature of at least 700° C. in the presence of oxygen. Also this method requires the reactor containing the deactivated catalyst to be taken out of operation and in view of the high temperature the catalyst needs to be discharged from the reactor to enable the regeneration. Moreover, this regeneration treatment is very energy-consuming, which is undesired from both an environmental and an economic perspective.

The present invention aims to overcome these disadvantages of the known regeneration methods.

Accordingly, the present invention in a further aspect relates to a process for re-activating an at least partly deactivated heterogeneous epoxidation catalyst capable of promoting the epoxidation reaction between an alkene and an organic hydroperoxide into alkylene oxide and an alcohol, which process comprises the steps of:
(1) reacting at least some organic hydroperoxide with alkene into alkylene oxide and an alcohol in the presence of a suitable heterogeneous epoxidation catalyst under suitable epoxidation conditions;
(2) contacting the at least partly deactivated catalyst with an epoxidation reaction mixture resulting from step (1) comprising the organic hydroperoxide, alkene, alkylene oxide and the alcohol, at a temperature, which is at least 5° C. higher than the final temperature at which the at least partly deactivated catalyst was in use directly before the start of the re-activation.

Advantages of the above process are (i) that the reactor containing the deactivated catalyst does not have to be taken out of operation each time the level of deactivation has become undesirably high and (ii) that the deactivated catalyst continues to contribute to the final alkylene oxide yield while being regenerated.

In order to attain an effective re-activation it is preferred that in step (1) of the above process a feed comprising the organic hydroperoxide and alkene is passed through at least two reactors which both contain a bed of heterogeneous epoxidation catalyst particles before the reaction mixture thus obtained in contacted with the at least partly deactivated catalyst in step (2).

It is preferred to carry out step (2) at a temperature, which is at least 10 and more preferably at least 15° C. higher than the final temperature at which the at least partly deactivated catalyst was in operation directly before the start of the re-activation. Suitably, however, the temperature during the reactivation will not be more than 50° C., more suitably not more than 30° C., higher than said final temperature. In order to attain an effective re-activation of the epoxidation catalyst it was found particularly suitable to continue the contacting between the at least partly deactivated catalyst and the reaction mixture in step (2) for at least 20 hours, preferably for at least 30 hours. The re-activation can stop as soon as the catalyst activity has been restored to the desired level. However, as has also been explained herein before, there is no fixed maximum to this time, because the reactor containing the catalyst to be reactivated remains in constant operation during the re-activation.

The re-activation has been found particularly effective for non-zeolitic epoxidation catalysts, more particularly for titanium-containing epoxidation catalysts. Of these the titania-on-silica catalysts are most suitably applied. However, other non-zeolitic heterogeneous epoxidation catalysts may be re-activated as well with the present method.

The alkene and organic hydroperoxide used are the same as described herein before in relation to the process for preparing propylene oxide. Accordingly, most preferably, the alkene used is propene, while the organic hydroperoxide is ethylbenzene hydroperoxide. These reactants result in the formation of propylene oxide and 1-phenylethanol.

The invention is further illustrated by the following examples without limiting the scope of the invention to these particular embodiments.

EXAMPLE 1

This example was carried out in a continuous epoxidation bench scale unit containing two vessels on automatic weight balances containing respectively the EBHP and alkene feed streams, two high pressure pumps, a fixed bed reactor, a third pump for pumping a recycle stream over the reactor, means to maintain the reactor continuously at temperatures between 60 and 120° C., a stripper to remove light boiling components like alkene, a cooler and a vessel for receiving the product.

The feeds were supplied to the reactor via the two high pressure pumps and mixed together before entering the reactor. The reactor was operated liquid full at 50 bara pressure. A large recycle stream was maintained over the reactor to have isothermal operation of the reactor bed and to ensure that the catalyst to be re-activated is contacted with epoxidation reaction product. The feed of alkene and a 35 wt % EBHP solution in ethylbenzene was mixed with the recycle stream prior to introduction into the reactor.

A compositional analysis of the reaction mixture was carried out by means of Super Critical Fluid Chromatography (SFC).

The following process conditions were maintained:
throughput EBHP solution: 30 grams/hour
throughput alkene: 18 grams/hour
recycle flow: 2.5 kg/hour.

The catalyst used in the reactor was a partly deactivated titanium/silica catalyst obtained from the epoxidation section of a commercial styrene/alkylene oxide co-production process.

The activity of the catalyst is expressed as "K85" indicating the reaction rate constant in $kg^2$ of liquid per kg of catalyst per mole per hour ($kg^2/(kg*mole*h)$) normalised at 85° C. assuming that first order reaction kinetics apply in EBHP and in propene.

The continuous epoxidation bench scale unit containing the partly deactivated titanium/silica catalyst was started up at runhour 0 at 90° C., the final temperature at which the titanium/silica catalyst was previously used in the epoxidation section of a commercial styrene/alkylene oxide co-production process. The unit was further operated under the conditions indicated above. At runhour 5 the reaction rate expressed as K85 was 0.2 $kg^2/(kg*mole*h)$. Albeit low, this reaction constant indicates that propylene oxide and 1-phenyl-ethanol were formed.

Then, at runhour 30, the temperature was increased from 90° C. to 110° C.

The increase in activity of the titanium/silica catalyst is indicated in Table I. K85 is expressed in $kg^2/(kg*mole*h)$.

TABLE I

| | Temperature reactivation | | | | | | | |
|---|---|---|---|---|---|---|---|---|
| Runhour | 5 | 15 | 30 | 50 | 65 | 80 | 100 | 150 |
| K85 | 0.2 | 0.2 | 0.2 | 1.0 | 1.5 | 2.5 | 3.0 | 3.0 |

From Table I it can be seen that contacting the deactivated catalyst with epoxidation reaction product and increasing the temperature with 20° C. from 90 to 110° C. at runhour 30 eventually results in an activity which is 15 times higher than the original activity of the deactivated catalyst.

Comparative Example 1

Example 1 was repeated except that the temperature was kept at 90° C. for 150 hours.

It was found that at runhours 50, 100 and 150 the K85 was 0.2 $kg^2/(kg*mole*h)$. Accordingly, the activity of the deactivated catalyst constantly remained low.

EXAMPLE 2

A bank of four serially connected epoxidation reactors, each having a volume of 9.2 $m^3$ and containing 4000 kg of titania-on-silica epoxidation catalyst was used in this experiment to illustrate the invention.

During the 36 hours of reactivation in this experiment the EBHP feed (35 wt % EBHP solution in ethylbenzene) and propene feed to the epoxidation reactor section were kept constant at respectively 100 tonnes/hr and 90 tonnes/hr. Accordingly, EBHP and propene conversion into propylene oxide and 1-phenyl-ethanol continued during the reactivation.

The bank of reactors had been in operation for several weeks and the activity of the catalyst in the first reactor had decreased to less than 1% of its original activity, which is the activity of fresh catalyst immediately after it has been loaded into the reactor. The outlet temperature of the first reactor was approximately 90° C., The first reactor was then switched to the terminal position. In this position the effluent from the third reactor was passed through the deactivated catalyst bed during 36 hours, said effluent having a temperature of 120° C.

The first order reaction rate constant of the epoxidation ($k_0$), as determined for the first order conversion of EBHP in the reactor containing the catalyst to be reactivated, was determined as a function of time and the results are indicated in Table II.

The reactor switch took place at t=0 hr. The activity of the deactivated catalyst, expressed as $ln(k_0)$, at that moment is indicated in the Table.

TABLE II

| Reactivation | | | | | | | | |
|---|---|---|---|---|---|---|---|---|
| time (h) | 0 | 1 | 5 | 10 | 20 | 25 | 30 | 36 |
| ln(k0) | 7.8 | 8.2 | 9.0 | 9.1 | 9.3 | 9.5 | 9.7 | 9.8 |

From table II it can be seen that the activity of the deactivated catalyst in the first reactor significantly increased by the treatment according to the present invention.

What is claimed is:

1. Process for the preparation of alkylene oxide, which process comprises passing a feed comprising an organic hydroperoxide and alkene through a bank of at least two serially connected reactors all containing a bed of heterogeneous epoxidation catalyst particles and operated in a cyclic mode, optionally followed by at least one additional epoxidation reactor containing a bed of heterogeneous epoxidation catalyst particles, and continuously withdrawing a product stream from the final epoxidation reactor comprising alkylene oxide and an alcohol as reaction products, from which product stream the alkylene oxide end-product is recovered, in which process:
   (a) the first reactor of the cyclically operated bank is put in a position further down this bank or in a position directly after any one of the additional reactors when the activity of the epoxidation catalyst contained therein has decreased to an undesirably low level;
   (b) in this position the catalyst with decreased activity is contacted with the effluent from the reactor in the preceding position at a temperature which is at least 5° C. higher than the final temperature at which the catalyst was in use in the first position of the bank and for sufficient time to restore its activity to the desired level.

2. Process as claimed in claim 1, wherein the cyclically operated bank consists of at least three serially connected epoxidation reactors.

3. Process as claimed in claim 1, wherein steps (a) and (b) are repeated until the activity of the catalyst to be re-activated can no longer be restored to the desired level.

4. Process as claimed in claim 1, wherein the first reactor of the bank containing the catalyst which is mostly deactivated, is taken out of operation, the deactivated catalyst is replaced by fresh catalyst after which this reactor is put back into operation in the terminal position of the bank.

5. Process as claimed in claim 1, which comprises the additional steps of:

(c) after the activity of the catalyst has been restored to the desired level, the reactor is put back in the first position of the bank;

(d) optionally steps (a) through (c) are repeated at least one time;

(e) the first reactor is taken out of operation when the activity of the epoxidation catalyst contained therein has decreased to an unacceptably low level and can no longer be restored to the desired level and the deactivated catalyst is replaced with fresh catalyst;

(f) this reactor is put back into operation in the terminal position of the cyclically operated bank; and (g) steps (a) through (f) are repeated while a product stream containing alkylene oxide and an alcohol is continuously withdrawn from the last reactor.

6. Process as claimed in claim 1, wherein the heterogeneous epoxidation catalyst used in all epoxidation reactors comprises a titanium-containing catalyst.

7. Process as claimed in claim 1, wherein the alkene used comprises propene and the organic hydroperoxide used comprises ethylbenzene hydroperoxide or tert-butyl hydroperoxide.

8. Process for re-activating an at least partly deactivated heterogeneous epoxidation catalyst capable of promoting the epoxidation reaction between an alkene and an organic hydroperoxide into alkylene oxide and an alcohol, which process comprises the steps of:

(1) reacting at least some organic hydroperoxide with alkene into alkylene oxide and an alcohol in the presence of a suitable heterogeneous epoxidation catalyst under suitable epoxidation conditions;

(2) contacting the at least partly deactivated catalyst with an epoxidation reaction mixture resulting from step (1) comprising the organic hydroperoxide, alkene, alkylene oxide and the alcohol, at a temperature, which is at least 5° C. higher than the final temperature at which the at least partly deactivated catalyst was in use directly before the start of the re-activation.

9. Process as claimed in claim 8, wherein in step (1) a feed comprising the organic hydroperoxide and alkene is passed through at least two reactors containing a bed of heterogeneous epoxidation catalyst particles before the reaction mixture thus obtained in contacted with the at least partly deactivated catalyst in step (2).

10. Process as claimed in claim 8, wherein step (2) is carried out at a temperature, which is at least 10° C. higher than the final temperature at which the at least partly deactivated catalyst was in operation directly before the start of the re-activation.

11. Process as claimed in claim 8, wherein the contacting between the at least partly deactivated catalyst and the reaction mixture in step (2) is continued for at least 20 hours, preferably at least 30 hours.

12. Process as claimed in claim 8, wherein the at least partly deactivated epoxidation catalyst comprises at titanium-containing catalyst.

13. Process as claimed in claim 8, wherein the organic hydroperoxide comprises ethylbenzene hydroperoxide and the alcohol formed is 1-phenylethanol.

14. Process as claimed in claim 1, wherein the heterogeneous epoxidation catalyst used in all epoxidation reactors comprises a titania-on-silica catalyst.

* * * * *